(12) United States Patent
Miyazaki et al.

(10) Patent No.: US 7,479,204 B2
(45) Date of Patent: Jan. 20, 2009

(54) METHOD OF MANUFACTURING SEMICONDUCTOR SUBSTRATE AND METHOD OF EVALUATING QUALITY OF SEMICONDUCTOR SUBSTRATE

(75) Inventors: Morimasa Miyazaki, Saga (JP);
Takafumi Kitamura, Saga (JP); Tetsuro Iwashita, Saga (JP); Mihoko Ohira, Saga (JP)

(73) Assignee: Sumco Corporation, Tokyo (JP)

( * ) Notice: Subject to any disclaimer, the term of this patent is extended or adjusted under 35 U.S.C. 154(b) by 0 days.

(21) Appl. No.: 11/564,374

(22) Filed: Nov. 29, 2006

(65) Prior Publication Data

US 2007/0193686 A1     Aug. 23, 2007

(30) Foreign Application Priority Data

Nov. 30, 2005   (JP) .............................. 2005-345403

(51) Int. Cl.
    *H01L 21/306* (2006.01)
(52) U.S. Cl. ...................... 156/345.1; 436/14
(58) Field of Classification Search .............. 156/345.1
    See application file for complete search history.

(56) References Cited

U.S. PATENT DOCUMENTS

| 5,946,543 A * | 8/1999 | Kimura et al. ............. 438/14 |
| 2002/0155630 A1 * | 10/2002 | Iwabuchi .................... 438/16 |
| 2004/0106217 A1 * | 6/2004 | Higgs ............................ 438/5 |
| 2006/0205325 A1 * | 9/2006 | Abe et al. ..................... 451/36 |

FOREIGN PATENT DOCUMENTS

| JP | 2000193597 A | * | 7/2000 |
| JP | 2000208469 A | * | 7/2000 |
| JP | 2000-102332 | | 4/2001 |

OTHER PUBLICATIONS

English Language Abstract of JP 2001-102332.

* cited by examiner

*Primary Examiner*—Matthew Smith
*Assistant Examiner*—Walter H Swanson
(74) *Attorney, Agent, or Firm*—Greenblum & Bernstein, P.L.C.

(57) ABSTRACT

A method of evaluating the presence or absence and/or degree of metal contamination of a semiconductor substrate including etching the surface of the semiconductor substrate by SC-1 cleaning and/or a HF cleaning, detecting bright points on the surface of the etched substrate with a foreign matter inspection device, and evaluating the presence or absence and/or degree of metal contamination of the semiconductor substrate based on the distribution pattern of bright points detected on the surface of the substrate. Also disclosed is a method of manufacturing a semiconductor substrate comprising mirror polishing a silicon wafer surface, wherein the mirror polishing is conducted using a slurry having a Cu content of approximately equal to or less than 10 ppb, a Ni content of approximately equal to or less than 10 ppb, and an Fe content of approximately equal to or less than 1,000 ppb, and evaluating the semiconductor substrate as above.

4 Claims, 6 Drawing Sheets

METHOD OF MANUFACTURING SEMICONDUCTOR SUBSTRATE AND METHOD OF EVALUATING QUALITY OF SEMICONDUCTOR SUBSTRATE

CROSS-REFERENCE TO RELATED APPLICATIONS

This application claims benefit of priority under 35 USC 119 to Japanese Patent Application No. 2005-345403 filed on Nov. 30, 2005, which is expressly incorporated herein by reference in its entirety.

BACKGROUND OF THE INVENTION

1. Field of the Invention

The present invention relates to a method of manufacturing a semiconductor substrate of reduced metal contamination and to a method of evaluating contamination and defects in a substrate.

2. Discussion of the Background

Generally, a semiconductor substrate serving as the base of a semiconductor part is manufactured by slicing to prescribed thickness a silicon single crystal ingot to fabricate a silicon wafer and then polishing one or both surfaces of the silicon wafer to a mirror finished surface with a mirror polishing device (for example, see Japanese Unexamined Patent Publication (KOKAI) No. 2001-102332, which is expressly incorporated herein by reference in its entirety).

An inspection method in which bright points detected on the surface of a semiconductor substrate with a foreign matter inspection device are observed has been proposed as a quality evaluation method for such wafers having a mirror finished surface. In this inspection method, particles on the substrate surface, Crystal Originated Particles (COPs), dislocations, various surface pits due to the quality of the substrate crystal, and the like are detected as bright points. Since particles on the substrate are observed as protrusions and surface pits are observed as indentations, the causes of bright points caused by particles and surface pits can be specified to an extent.

However, in wafers of which surfaces have been subjected to mirror polishing, there is a problem in that metal ions contained in the slurry used in mirror polishing diffuse into the wafer during mirror polishing, contaminating the bulk near the surface. In such metal-contaminated wafers, crystal defects and surface roughness occur on the surface, compromising quality. Thus, there is a need for a method for providing a semiconductor substrate with reduced metal contamination.

Further, since crystal defects and surface roughness caused by metal contamination of the bulk as set forth above do not appear as protrusions and indentations on the substrate surface, they are normally not detected as bright points in the inspection with foreign matter inspection devices, and run the risk of being supplied as a nondefective product.

SUMMARY OF THE INVENTION

A feature of the present invention provides for a semiconductor substrate with reduced metal contamination.

A feature of the present invention further provides for evaluating various defects caused by metal contamination in semiconductor substrates.

Slurries employed in mirror polishing of silicon wafers generally contain various metal ions. These metal ions diffuse into the interior of the wafer during the mirror polishing step, contaminating the interior of the finished product substrate. However, in practice, it is impossible to completely eliminate metal ions in the manufacturing of a slurry. Accordingly, the present inventors studied in great detail the relation between the concentration of metals contained in slurries and metal contamination in order to reduce metal contamination of the semiconductor substrate following mirror polishing, particularly contamination of the bulk near the surface. As a result, they discovered that when mirror polishing was conducted with a slurry having a Cu content and an Ni content of approximately equal to or less than 10 ppb each and an Fe content of approximately equal to or less than 1,000 ppb, metal contamination of the interior of the substrate was markedly reduced.

Further, the present inventors conducted extensive research into evaluating the various defects caused by metal contamination of the interior of the substrate. This resulted in the discovery that by conducting SC-1 cleaning (Standard Clean 1—typically a mixture of $NH_4OH$, $H_2O_2$, and deionized water in an approximate ratio of 1:1:5, however other ratios are contemplated by the present invention) and/or Fluoric acid (HF) cleaning to selectively etch the substrate surface, contaminant metals in the substrate could be detected as bright points by a foreign matter inspection device.

The present invention was devised on this basis.

A feature of the present invention relates to a method of manufacturing a semiconductor substrate including mirror polishing a silicon wafer surface, wherein the mirror polishing is conducted using a slurry having a Cu content of approximately equal to or less than 10 ppb, a Ni content of approximately equal to or less than 10 ppb, and an Fe content of approximately equal to or less than 1,000 ppb.

A feature of the present invention further relates to a method of evaluating a quality of a semiconductor substrate including etching the surface of the semiconductor substrate by SC-1 cleaning and/or a HF cleaning, detecting bright points on the surface of the etched substrate with a foreign matter inspection device, and evaluating the quality of the semiconductor substrate based on the bright points detected on the surface of the substrate.

A feature of the present invention still further relates to a method of manufacturing a semiconductor substrate including preparing a product lot of semiconductor substrate having plural semiconductor substrates, extracting at least one semiconductor substrate from the lot, evaluating the quality of the semiconductor substrate that has been extracted, when the semiconductor substrate that has been extracted is determined as a nondefective product in the evaluation, supplying, as a finished product, a semiconductor substrate comprised in the lot from which the semiconductor substrate determined as a nondefective product has been extracted, wherein the product lot is manufactured by the above-mentioned method of manufacturing a semiconductor substrate, and the evaluation of the extracted semiconductor substrate is conducted by the above-mentioned method of evaluating a quality of a semiconductor substrate According to the present invention, a high-quality semiconductor substrate of reduced metal contamination can be provided by preventing metal contamination in the mirror polishing step in advance.

Based on the present invention, it is possible to evaluate various defects caused by metals in semiconductor substrates, eliminate as defective product lots that are contaminated by metals, and selectively supply high-quality lots of finished product.

Other exemplary embodiments and advantages of the present invention may be ascertained by reviewing the present disclosure and the accompanying drawings.

BRIEF DESCRIPTION OF THE DRAWINGS

The present invention will be described in the following text by the exemplary, non-limiting embodiments shown in the figures, wherein.

DESCRIPTIONS OF THE EMBODIMENTS

Figure 1:
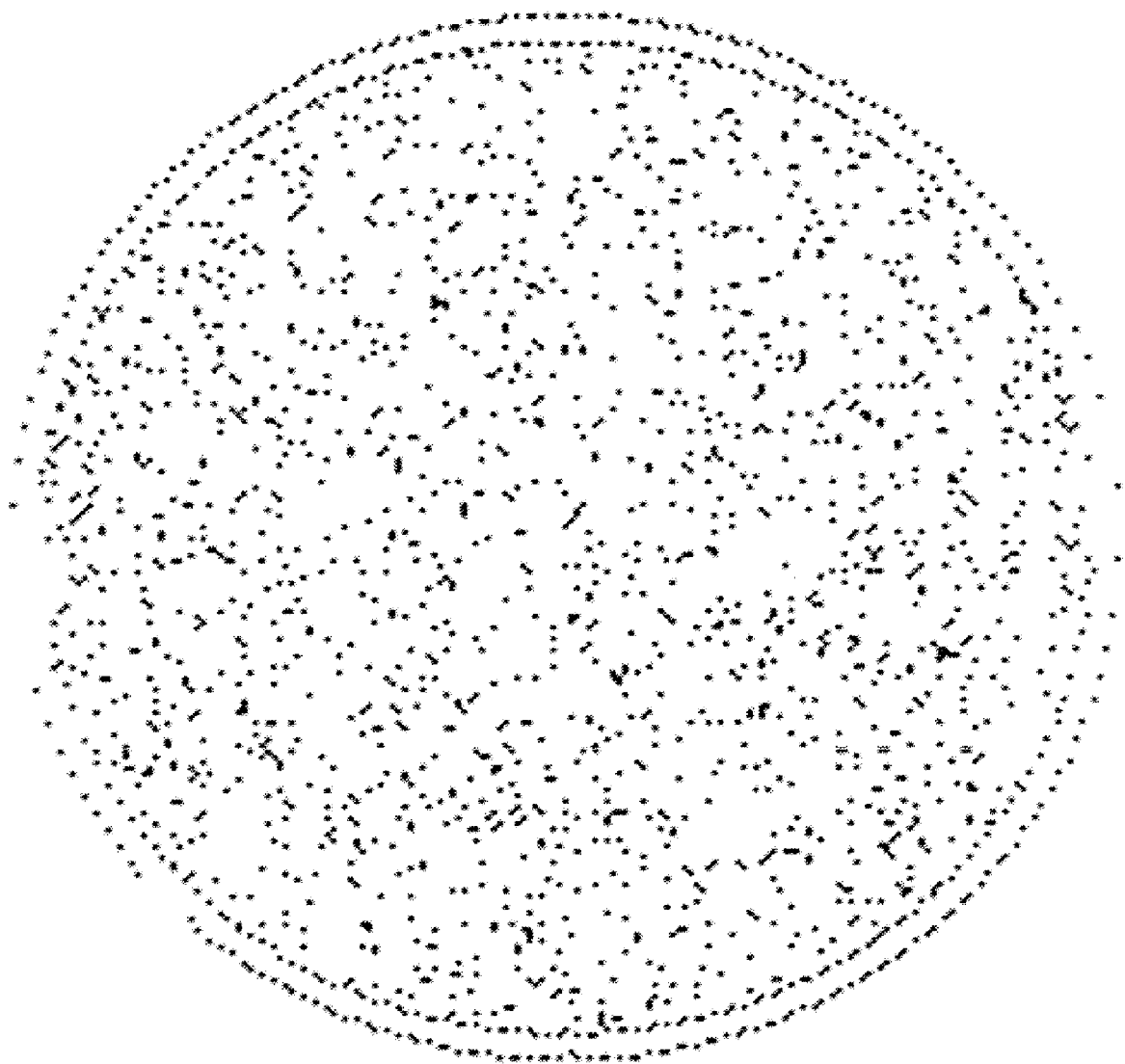
FIG. 1 shows a distribution pattern of bright points of sample 1 in Example 2.
Figure 2:
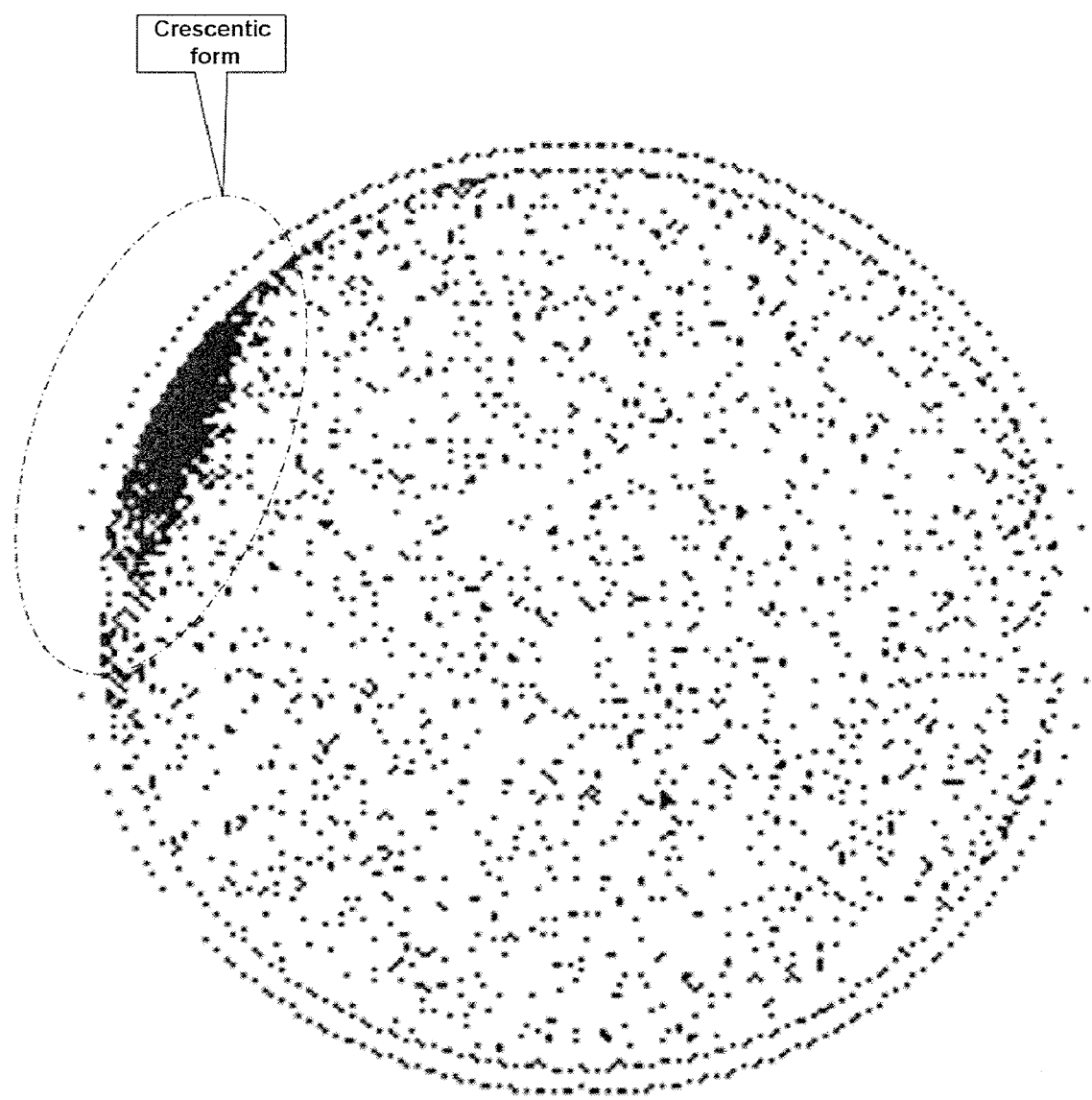
FIG. 2 shows a distribution pattern of bright points of sample 2 in Example 2.
Figure 3:
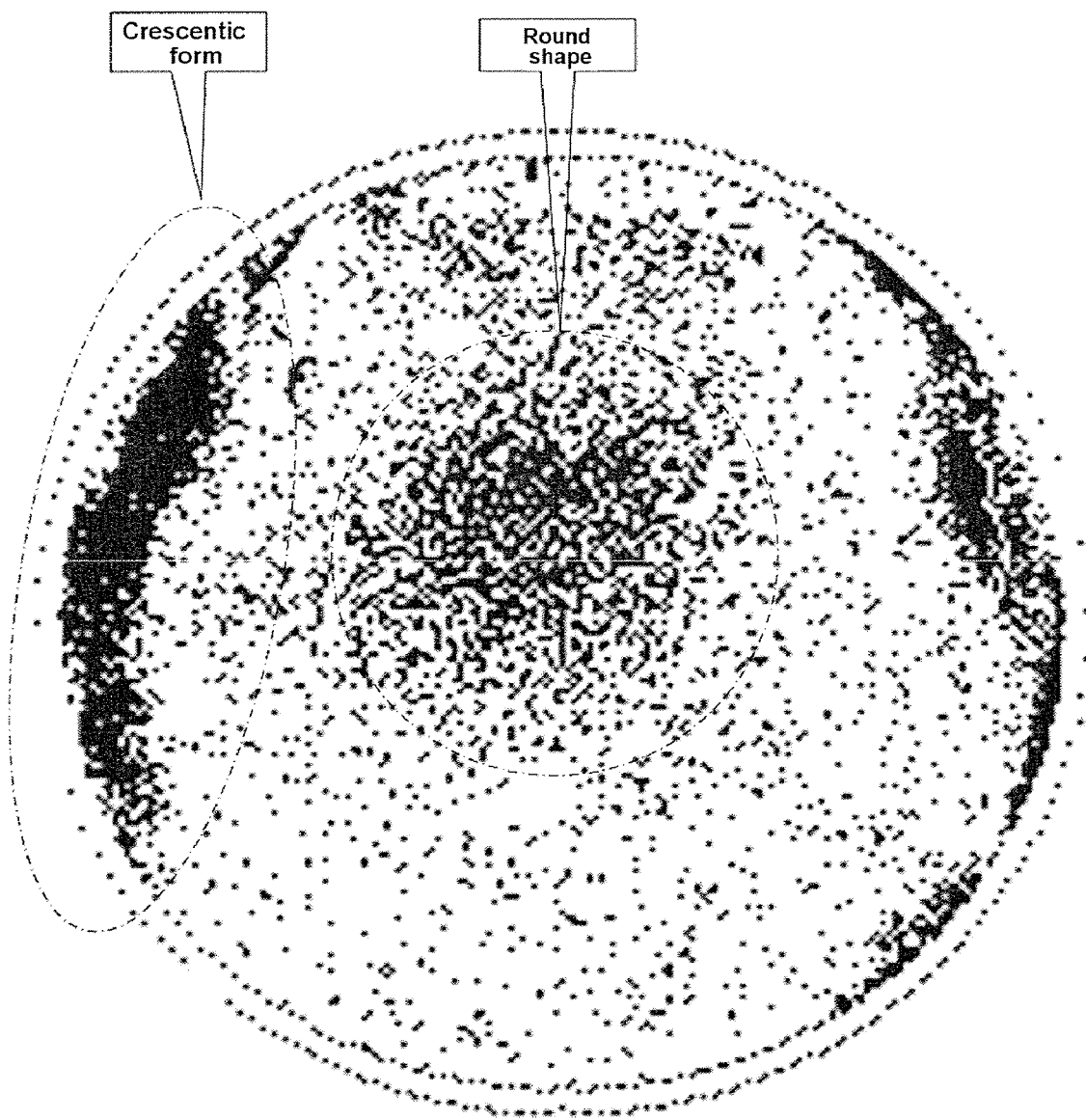
FIG. 3 shows a distribution pattern of bright points of sample 3 in Example 2.
Figure 4:
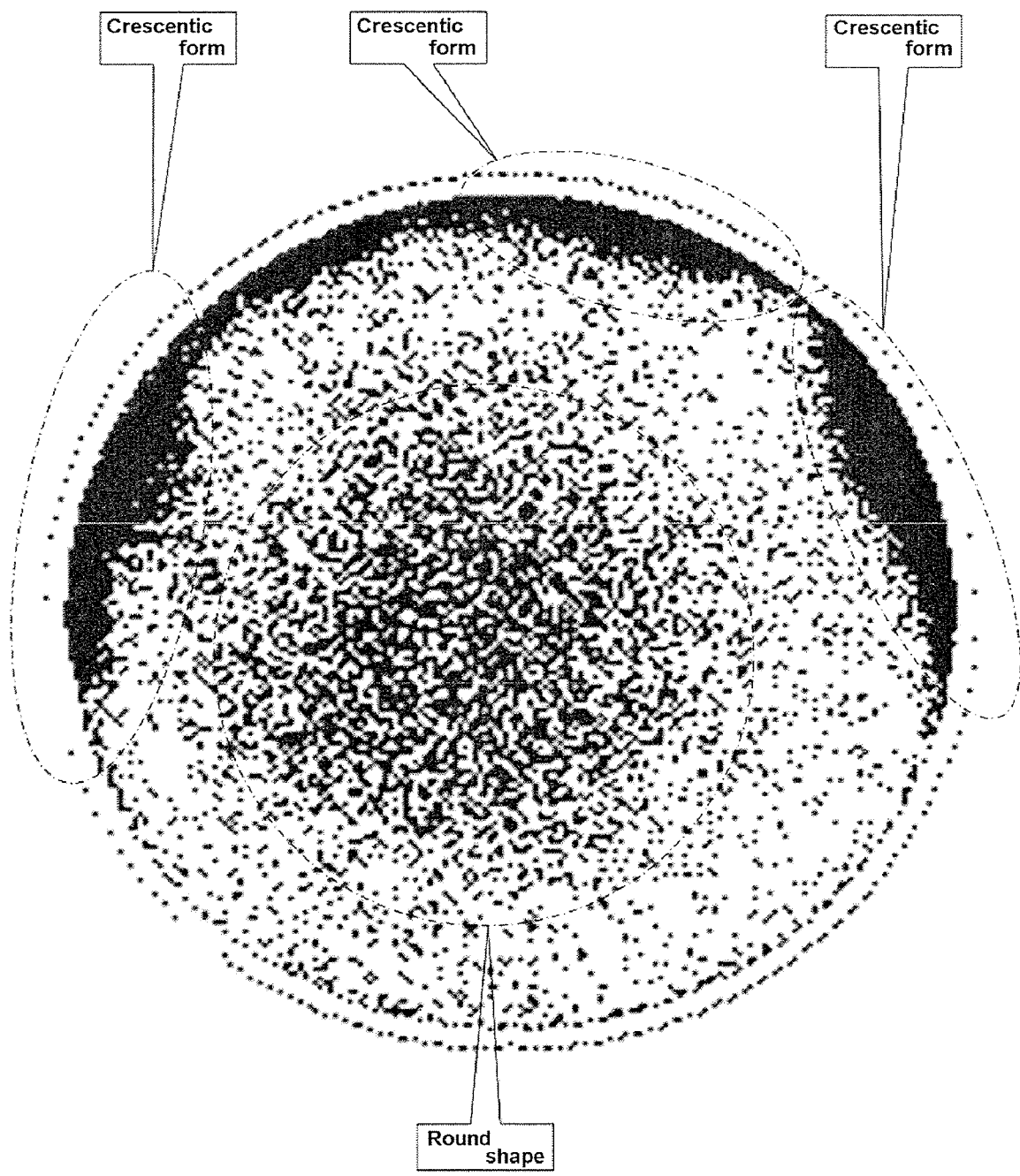
FIG. 4 shows a distribution pattern of bright points of sample 4 in Example 2.

The following preferred specific embodiments are, therefore, to be construed as merely illustrative, and not limitative of the remainder of the disclosure in any way whatsoever. In this regard, no attempt is made to show structural details of the present invention in more detail than is necessary for the fundamental understanding of the present invention, the description taken with the drawings making apparent to those skilled in the art how the several forms of the present invention may be embodied in practice.

The method of manufacturing a semiconductor substrate of the present invention includes mirror polishing a silicon wafer surface, wherein the mirror polishing is conducted using a slurry having a Cu content of approximately equal to or less than 10 ppb, a Ni content of approximately equal to or less than 10 ppb, and an Fe content of approximately equal to or less than 1,000 ppb.

In the above slurry, the Cu content is approximately equal to or less than 10 ppb, the Ni content is approximately equal to or less than 10 ppb, and the Fe content is approximately equal to or less than 1,000 ppb. When the Cu, Ni, and Fe content respectively exceed the above-stated range, the interior of the semiconductor substrate of which surface has been subjected to mirror polishing is contaminated with metal, causing surface defects and surface roughness and compromising quality.

The Cu content of the above slurry is desirably approximately equal to or less than 5 ppb. The Cu content of the slurry is optimally approximately 0 ppb.

The Ni content of the above slurry is desirably approximately equal to or less than 5 ppb. The Ni content of the slurry is optimally approximately 0 ppb.

The Fe content of the above slurry is desirably approximately equal to or less than 50 ppb. The Fe content of the slurry is optimally approximately 0 ppb.

The above slurry can be a known slurry conventionally used in mirror polishing for wafer, such as a slurry obtained by adding a chelating agent such as ethylenediaminetetracetic acid to an alkali solution containing silica particles to reduce the metal ion content. The slurries employed in conventional mirror polishing are often repeatedly employed a number of times. This repeated use tends to increase the metal ion content. Accordingly, it is effective for reducing the metal ion content not to repeatedly employ the slurry; that is, use it once and then discard it.

Silicon wafers to be subjected to mirror polishing are not specifically limited. For example, a silicon single crystal ingot can be sliced to prescribed thickness to obtain a silicon wafer for use.

The above silicon wafer is then mirror polished using the above slurry. The mirror polishing method is not specifically limited; a dual-surface polishing method such as lapping, a single-wafer method, a wax-free polishing method, a wax mount batch-type single-surface polishing method, and other known methods may be employed.

In the present invention, a product lot comprised of plural semiconductor substrates can be prepared by the above method to mass produce plural semiconductor substrates of low metal contamination.

At least one semiconductor substrate can be extracted from the product lot for evaluation, the quality of the semiconductor substrate that has been extracted can be evaluated, and when the evaluated semiconductor substrate is determined as a nondefective product, other semiconductor substrates in the same lot as the semiconductor substrate that has been determined as a nondefective product can be supplied as a finished product to provide high-quality semiconductor substrates.

The above evaluation can be conducted by a method of evaluating a quality of a semiconductor substrate including etching the surface of the semiconductor substrate by SC-1 cleaning and/or a HF cleaning, detecting bright points on the surface of the etched substrate with a foreign matter inspection device, and evaluating the quality of the semiconductor substrate based on the bright points detected on the surface of the substrate.

The above evaluation method will be described below.

The above evaluation is conducted by SC-1 cleaning and/or HF cleaning to etch the semiconductor substrate and then employing a foreign matter inspection device to detect bright points on the etched surface. By SC-1 cleaning and/or HF cleaning, metals contaminating the bulk in the vicinity of the substrate surface can be selectively etched, thereby causing crystal defects and surface roughness causing metal contamination to appear on the etched surface. Thus, by employing a foreign matter inspection device to detect bright points on the etched surface, the crystal defects and surface roughness can be detected as bright points.

The above etching may be conducted as one or more SC-1 cleanings, or may be conducted as one or more HF cleanings. It is also possible to combine SC-1 cleaning and HF cleaning. The etching depth is desirably suitably adjusted to permit the selective etching of metals contaminating the bulk near the surface of the substrate. For example, when employing SC-1 cleaning, the etching depth can be from approximately 300 to approximately 3,000 nm. When employing HF cleaning, an etching depth of even about 0 nm can selectively etch away metals contaminating the bulk near the substrate surface. The cleaning solution employed in SC-1 cleaning is not specifically limited; a known solution may be employed. The HF solution employed in HF cleaning is not specifically limited; a known solution may be employed, and an HF aqueous solution with a concentration of approximately 0.5 to approximately 5 volume percent is desirably employed.

In the above evaluation method, quality evaluation on the etched substrate surface is conducted based on the detection of bright points by a foreign matter inspection device. Specifically, the presence or absence of metal contamination and/or the degree of the contamination can be evaluated based on the number and/or distribution pattern of the bright points. The bright points that are detected following etching are thought to be crystal defects and/or surface roughness caused by metal contamination of the bulk near the substrate surface. Accordingly, the greater the number of bright points in the surface, the more crystal defects and/or surface roughness there are, indicating a high level of metal contamination.

In the above evaluation method, the bright points detected by the foreign matter inspection device are desirably observed by Scanning Electron Microscope (SEM) and/or Atomic Force Microscope (AFM). Thus, based on the shape of the bright points observed, the presence or absence of metal contamination can be determined with greater reliability and the type of metal contamination can be deduced. For example, in a map of bright points detected by a foreign matter inspection device, observation of an abnormal portion of concentrated bright points by SEM and/or AFM makes it possible to determine whether the abnormal portion is a collection of pits or the like. Further, when the shape of bright points observed by SEM or AFM, for example, possesses an orientation of <100>, which is the orientation in which copper silicide forms, it can be deduced that the bulk near the substrate surface has been contaminated with copper.

In the present invention, by supplying semiconductor substrates, as finished product substrates, in the same lot as a semiconductor substrate that has been determined as a nondefective product in the above evaluation, it is possible to reliably provide high-quality finished product semiconductor substrates. The criteria for determining nondefective products can be set in consideration of the physical properties required of the wafer based on the application and the like of the wafer.

Further, in the present invention, it is also possible to detect bright points with a foreign matter inspection device on the surface of an unetched substrate prior to the above quality evaluation following etching. In that case, particles on the substrate surface, COPs, and the like are detected as bright points. Normally, a product is determined as a nondefective product when the total number of bright points detected is equal to or less than approximately 3,000 on an eight-inch wafer and equal to or less than approximately 6,700 on a twelve-inch wafer. However, these determination criteria can be suitably varied based on the application or the like of the semiconductor substrate. In some substrate applications, it suffices to control just such surface contamination and surface defects. In such cases, it is possible to conduct just the above quality evaluation without conducting the above postetching quality evaluation. It is possible to provide highquality wafers with little contamination and few defects both with regard to surface and bulk by combining the above evaluation with the above post-etching quality evaluation.

EXAMPLES

The present invention will be described in detail below based on examples. However, the present invention is not limited to the examples.

Example 1

Four eight-inch sliced silicon wafers were mirror polished with a slurry. Different slurries were employed for each wafer. Table 1 shows the results of measurement of the Cu, Ni, and Fe contents of each slurry by the atomic absorption method. The metal ions in slurry 1 were reduced by the addition of ethylenediaminetetraacetic acid.

TABLE 1

|  | Cu (ppb) | Ni (ppb) | Fe (ppb) |
| --- | --- | --- | --- |
| Slurry 1 | 10 | 10 | 1,000 |
| Slurry 2 | 10 | 100 | 1,000 |
| Slurry 3 | 100 | 10 | 1,000 |
| Slurry 4 | 10 | 10 | 8,000 |

The silicon wafer subjected to mirror polishing with slurry 1 was denoted as sample 1, the silicon wafer subjected to mirror polishing with slurry 2 was denoted as sample 2, the silicon wafer subjected to mirror polishing with slurry 3 was denoted as sample 3, and the silicon wafer subjected to mirror polishing with slurry 4 was denoted as sample 4.

Table 2 shows the results obtained when each of the samples was inspected for particles with a foreign matter inspection device. In ordinary particle inspection, with respect to an eight-inch wafer, the wafer on which the total number of bright points is equal to or less than 3,000 is determined as a nondefective product. As shown in Table 2, all of the samples passed the particle inspection.

TABLE 2

|  | Total number of bright points |
| --- | --- |
| Sample 1 | 803 |
| Sample 2 | 839 |
| Sample 3 | 845 |
| Sample 4 | 761 |

Example 2

All of the samples prepared in Example 1 were inspected for metal contamination by the following method.

First, SC-1 cleaning was continuously conducted five times with a cleaning solution ($NH_4OH:H_2O_2:H_2O=1:1:5$) employed in SC-1 cleaning.

Next, the total number and the distribution pattern of bright points for each sample were measured with a foreign matter inspection device. The results are given in Table 3 and FIGS. 1 to 4. Table 3 shows the total number of bright points in each sample. FIGS. 1 to 4 show the distribution patterns of bright points in each sample. Taking into account the passing standard in particle inspection, samples with a total number of bright points not exceeding 3,000 were determined as a nondefective product.

TABLE 3

|  | Total number of bright points |
| --- | --- |
| Sample 1 | 1722 |
| Sample 2 | 4415 |
| Sample 3 | Equal to or greater than 30,000 |
| Sample 4 | Equal to or greater than 30,000 |

As indicated in Table 3, even among samples that passed the particle inspection, a metal contamination inspection revealed that metal contamination of the surface occurred due to slurries employed in the mirror polishing step.

As indicated in FIGS. 1 to 4, the distribution of bright points was found to vary based on the slurry employed in the mirror polishing step. In particular, in the sample shown in FIG. 2, the distribution pattern of bright points is a crescentic form. In the samples shown in FIGS. 3 and 4, the distribution patterns of the bright points comprise both round shape and crescentic form. From such distribution pattern, it reveals that portions contaminated by metals were concentrated.

The round and crescentic-shaped distribution patterns of the bright points are thought to be caused by the formation of defects due to metals in the mirror polishing step.

Accordingly, in the metal contamination inspection, wafers in which the distribution patterns of the bright points were locally concentrated, such as crescentic form and round shape, were determined to be defective.

From the above results, it reveals that metal contamination of the silicon wafer surface was seldom observed when a slurry with a Cu content and a Ni content each approximately equal to or less than 10 ppb and an Fe content of approximately equal to or less than 1,000 ppb was employed.

Example 3

Figure 5:
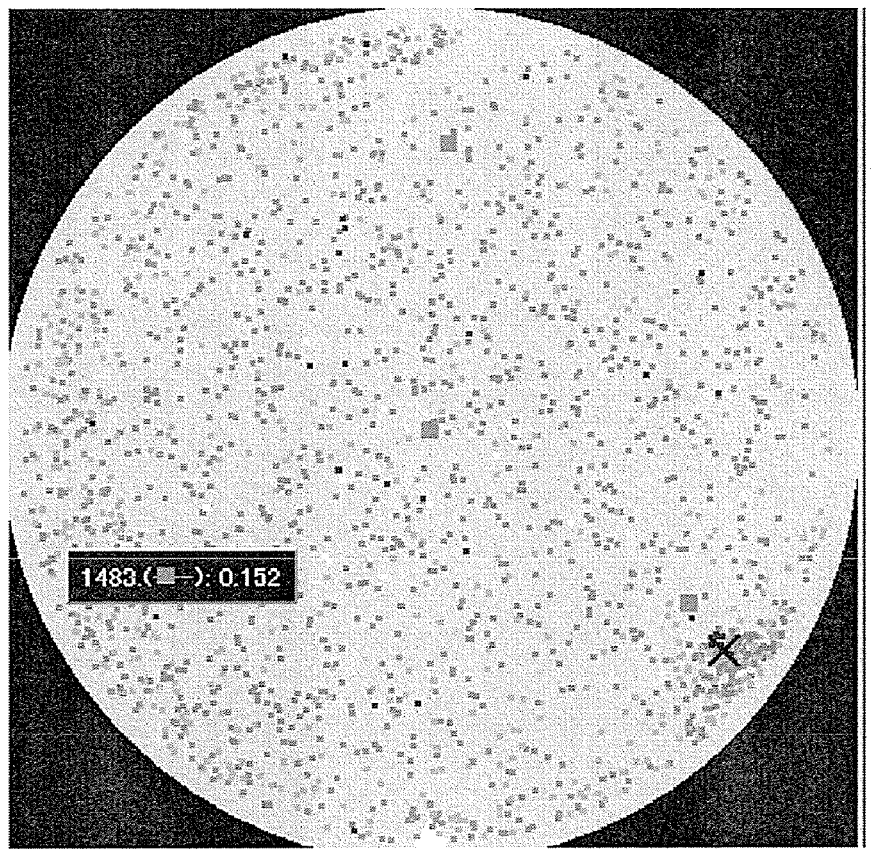
FIG. 5 shows a map of bright points on the substrate in Example 3.

The surfaces of silicon wafers following mirror polishing were etched by being continuously SC-1 cleaned three times with a cleaning solution ($NH_4OH:H_2O_2:H_2O=1:1:5$) employed in SC-1 cleaning. A foreign matter inspection device was employed to detect bright points on the surfaces thereof; the results are given in FIG. 5. As indicated in FIG. 5, an abnormal portion (the "X" portion in FIG. 5) in which bright points were densely packed was observed in the peripheral portion in a map of bright points observed by the foreign matter inspection device. Then, this peculiar pattern was observed by scanning electron microscopy (SEM). The results are given in FIG. 6.

Figure 6:
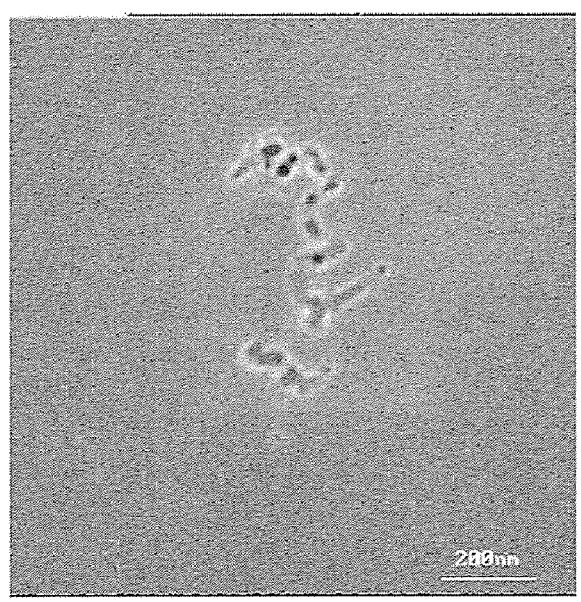
FIG. 6 shows an SEM photograph of the X portion of FIG. 5.

In the results of SEM observation as shown in FIG. 6, the abnormal portion was found to be a collection of pits. Observation at greater magnification revealed each pit to have a <100> orientation. On this basis, the pits were presumed to have been caused by Cu.

Example 4

Figure 7:
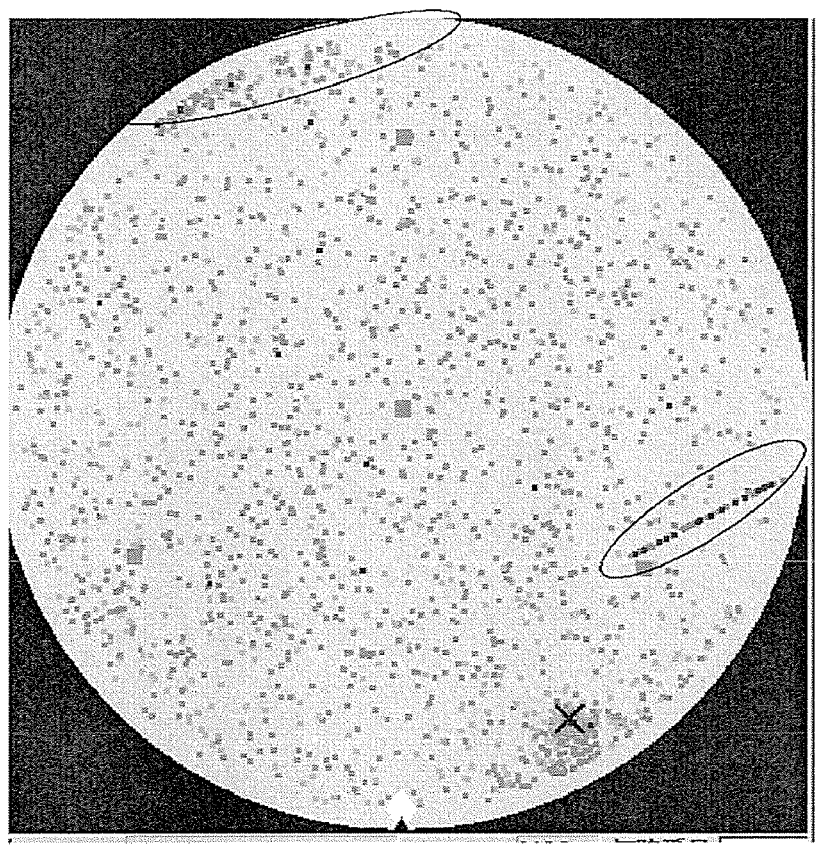
FIG. 7 shows a map of bright points on the surface in Example 4.

The surfaces of silicon wafers following mirror polishing were etched by being continuously SC-1 cleaned three times with a cleaning solution ($NH_4OH:H_2O_2:H_2O=1:1:5$) employed in SC-1 cleaning. A foreign matter inspection device was employed to detect bright points on the surfaces thereof; the results are given in FIG. 7. As indicated in FIG. 7, an abnormal portion (the elliptic portion in the lower right part of FIG. 7) in which bright points were densely packed in lines was observed in the peripheral portion in a map of bright points observed by the foreign matter inspection device. Then, this peculiar pattern was observed by scanning electron microscopy (SEM). The results are given in FIG. 8.

Figure 8:
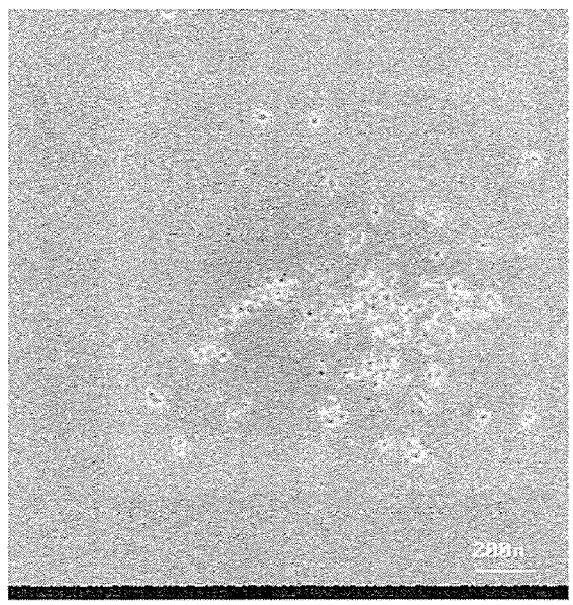
FIG. 8 shows an SEM photograph of the elliptic portion in the lower right part of FIG. 7.

As shown in FIG. 8, the results of SEM observation revealed that the abnormal linear portions were a collection of pits. Observation at greater magnification revealed each pit to have a <100> orientation. On this basis, the pits were presumed to have been caused by Cu. In FIG. 7, light reflected irregularly off the abnormal portion in the elliptic portion in the upper left part. Thus, this portion could be determined to have surface roughness. As in Example 3, in the "X" portion, each pit had a <100> orientation, so the pits were presumed to have been caused by Cu.

According to the present invention, a high-quality semiconductor substrate with reduced metal contamination can be provided.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of evaluating a presence or an absence and/or a degree of metal contamination of a semiconductor substrate comprising:
    etching the surface of the semiconductor substrate by SC-1 cleaning and/or a HF cleaning;
    detecting bright points on the surface of the etched substrate with a foreign matter inspection device; and
    evaluating the presence or absence and/or degree of metal contamination of the semiconductor substrate based on a distribution pattern of the bright points detected on the surface of the substrate.

2. The method of claim 1, wherein said evaluation is conducted based on the number and distribution pattern of the detected bright points.

3. The method of claim 1, wherein said evaluation further comprises observing the bright points, that have been detected with the foreign matter inspection device, with a scanning electron microscope and/or an atomic force microscope, and deducing the type of metal contamination based on the shape of the distribution pattern of the bright points observed with a scanning electron microscope and/or an atomic force microscope.

4. A method of manufacturing a semiconductor substrate comprising:
    preparing a product lot of semiconductor substrate having plural semiconductor substrates;
    extracting at least one semiconductor substrate from the lot;
    evaluating quality of the semiconductor substrate that has been extracted;
    when the semiconductor substrate that has been extracted is determined as a nondefective product in said evaluation, supplying, as a finished product, a semiconductor substrate comprised in the lot from which the semiconductor substrate determined as a nondefective product has been extracted, wherein
    the product lot is manufactured by a method comprising mirror polishing a silicon wafer surface, wherein said mirror polishing is conducted using a slurry having a Cu content of approximately equal to or less than 10 ppb, a Ni content of approximately equal to or less than 10 ppb, and an Fe content of approximately equal to or less than 1,000 ppb, and said evaluation of the extracted semiconductor substrate is conducted by the method of claim 1.

* * * * *